United States Patent [19]

Sacks

[11] Patent Number: 4,561,857
[45] Date of Patent: Dec. 31, 1985

[54] INTRAVENOUS FILTER RETAINER

[76] Inventor: Norman L. Sacks, 24502 Kings Rd., Laguna Niguel, Calif. 92677

[21] Appl. No.: 476,595

[22] Filed: Mar. 18, 1983

[51] Int. Cl.$^4$ .............................................. A61M 5/00
[52] U.S. Cl. .................................... 604/174; 604/179; 128/DIG. 6
[58] Field of Search ........................ 604/174, 179–180, 604/195, 252, 406; 128/DIG. 6, DIG. 26

[56] References Cited

U.S. PATENT DOCUMENTS

| | | | |
|---|---|---|---|
| 2,727,512 | 12/1955 | Muller | 128/DIG. 6 |
| 3,194,235 | 7/1965 | Cooke | 604/180 |
| 3,630,195 | 12/1971 | Santomieri | 604/180 |
| 3,782,377 | 1/1974 | Rychlik | 604/180 |
| 3,900,026 | 8/1975 | Wagner | 604/174 |
| 3,901,226 | 8/1975 | Scardenzan | 128/DIG. 6 |
| 3,918,446 | 11/1975 | Buttaravoli | 604/180 |
| 4,066,556 | 1/1978 | Vaillancourt | 604/190 |
| 4,198,989 | 4/1980 | Hawke et al. | 128/DIG. 26 |
| 4,336,806 | 6/1982 | Eldridge, Jr. | 604/174 |

Primary Examiner—C. Fred Rosenbaum
Assistant Examiner—Gene B. Kartchner
Attorney, Agent, or Firm—Poms, Smith, Lande & Rose

[57] ABSTRACT

A very lightweight intravenous filter retainer assembly, weighing only in the order of two grams, includes a formed medically inert plastic sheet element, Velcro tabs mounted on the side edges of this formed plastic sheet member and a foam strip for extending around the arm and engaging the Velcro tabs. The standard type of intravenous filter is an elongated generally rectangular element with one flat side and the other side having a central raised passageway and a pair of transverse grooves. The filter retainer assembly includes the formed plastic sheet material contoured to include a recess which extends over the back of the filter and further includes a pair of ridges to engage the recesses on the filter. In addition, the outer sides or edges of the plastic sheet element may be provided with longitudinally extending grooves to hold the intravenous tubing in a desired location relative to the patient's limb.

7 Claims, 6 Drawing Figures

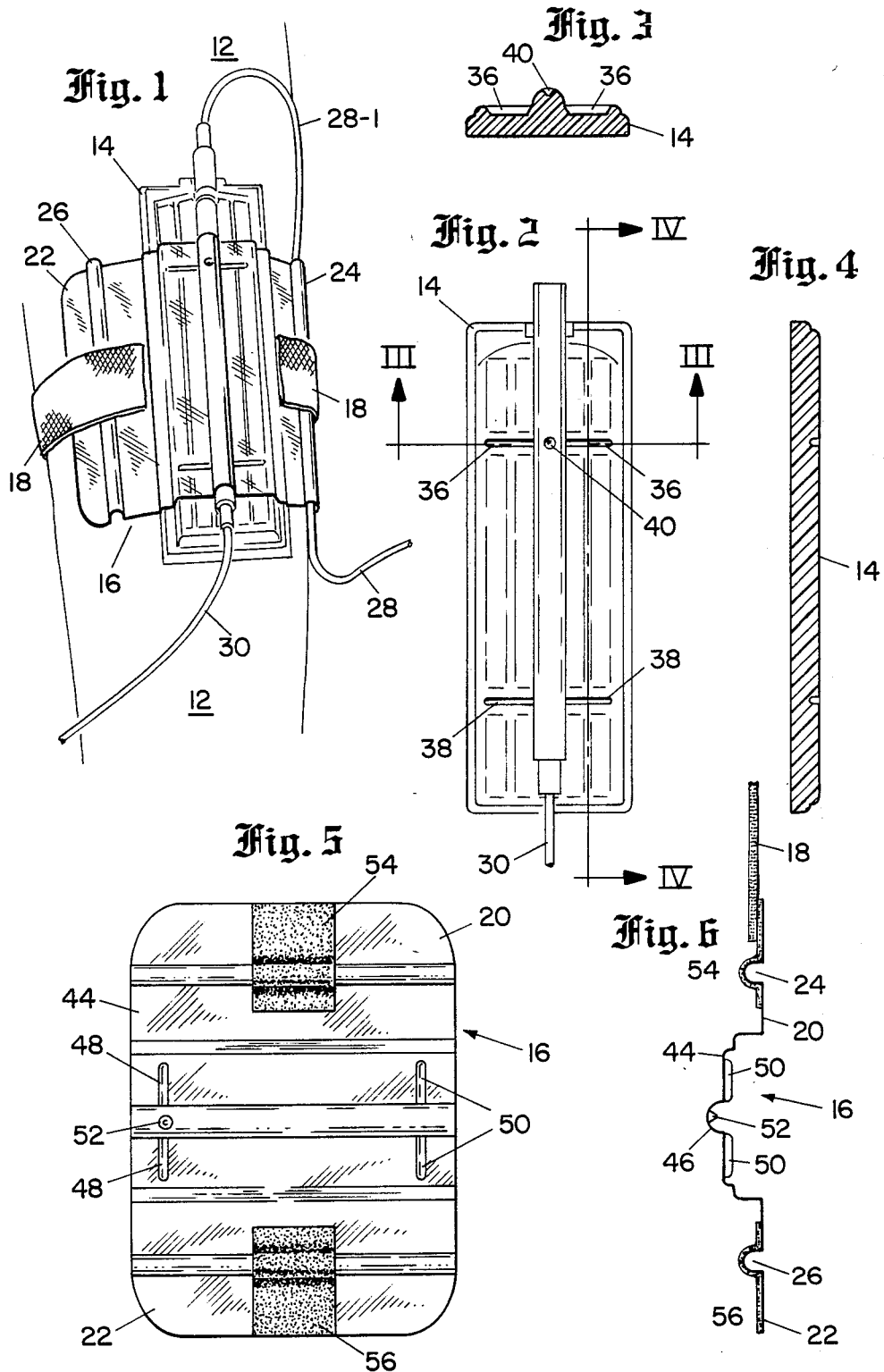

INTRAVENOUS FILTER RETAINER

FIELD OF THE INVENTION

This invention relates to intravenous filter arrangements for mounting on a patient's arm or leg.

BACKGROUND OF THE INVENTION

Intravenous filters, as they have been used heretofore, have often merely been included in the intravenous line without any special supporting arrangements, or they have been taped to the patient's arm. In the first case, when the filter is not held in place, it may become caught between the patient's arm and the bed clothing or other objects, and pull on the tubing, causing discomfort or possibly interruption of the flow of the intravenous fluid. On the other hand, when adhesive tape is wrapped around a patient's arm to hold the filter in place, the limb may be unduly constricted, which can injure the patient in the event of infiltration, or rapid swelling of a limb.

Accordingly, a principal object of the present invention is to provide a simple, inexpensive and lightweight intravenous filter retaining assembly, which will also readily break free in the event of infiltration or swelling of the limb, thus avoiding injury which might otherwise occur to the patient in the event of rigid constriction.

SUMMARY OF THE INVENTION

In accordance with a specific illustrative embodiment of the invention, an intravenous filter retaining assembly may include a thin piece of medically inert formed sheet plastic material having a central recessed portion with a configuration conforming to the outer configuration of the filter and at least one inner transverse ridge or detent to fit into the transverse groove or grooves of the filter to hold the filter into the retainer. In addition, the outer edges of the sheet material may be provided with small Velcro tabs, and a foam band having matching material is provided to extend around the arm of the patient and to secure to the Velcro tabs on the sheet plastic element.

In accordance with other features of the invention, the two outwardly extending portions of the plastic sheet element may be provided with longitudinally extending grooves to match the diameter of intravenous tubing which may be employed. In addition, the plastic sheet material may be made of medically inert approved plastic material, such as P. E. T. or polyethylene terephthalate glycol. Such plastic sheet material is available from many sources including Lustro Plastics of Valencia, Calif. The entire filter retaining assembly using this thin sheet material, weights substantially less than one quarter of an ounce.

In accordance with a broader aspect of the invention a thin piece of medically inert formed sheet material has an inner recess conforming to the outer configuration of an intravenous filter, and is provided with releasable strap securing arrangements to permit release of the unit upon infiltration of swelling of the limb.

The very lightweight nature of the units and their resultant relatively low cost and convenience of use, as well as lack of inconvenience to the patient are particular advantages of the present invention. Each of the units weigh in the order of two grams, or less than one-tenth of an ounce. Also, when these units are employed, the intravenous filter may be appropriately mounted in a convenient location toward the outside of the limb, and the likelihood of inadvertent rubbing of the filter between the patient's limb and the bed clothes and resultant strain or pulling on the intravenous tubing is avoided. Further, through the use of the supplemental grooves toward the edges of the filter element, the orientation and control of the intravenous tubing supply is conveniently handled.

Other objects, features, and advantages of the invention will become apparent from a consideration of the following detailed description and from the accompanying drawings.

BRIEF DESCRIPTION OF THE DRAWINGS

FIG. 1 shows an intravenous filter held onto a patient's arm using a retainer assembly illustrating the principles of the present invention;

FIGS. 2, 3 and 4 show a standard type of intravenous filter; and

FIGS. 5 and 6 are detailed plan and side views, respectively, of the filter retaining assembly per se.

DETAILED DESCRIPTION

FIG. 1 shows a patient's arm 12, an intravenous filter 14, the intravenous filter retainer assembly including a formed element of plastic sheet material 16, and a foam band 18. Although it is difficult to observe this feature in FIG. 1, the two laterally extending portions 20 and 22 of the plastic sheet material element, are provided with longitudinally extending grooves or recesses 24 and 26 which are useful in orienting the tubing 28 through which the intravenous fluid flows. It is also noted that the input intravenous fluid flows through the tubing 28 including the section 28-1 to the upper end of the filter unit 14 and from the output of the filter 14 through the tubing 30 to a catheter (not shown) which is employed in supplying the intravenous liquid to the patient.

The most widely used type of intravenous filter is made by the Pall Filter Company of Glencove, N.Y., and the configuration of the intravenous filter made by this company is shown in some detail in FIGS. 2, 3 and 4. FIG. 3 is a cross-sectional view taken along lines III—III of FIG. 2; and similarly, the cross-sectional view of FIG. 4 is taken along lines IV—IV of FIG. 2. In FIG. 2, the input 32 to the filter appears at the top, and a raised passageway 34 extends along the back of the filter 14, and the output tube 30 is secured to the lower end of the filter unit 14. The back of the filter is provided with two transverse recesses 36 and 38, and the tube 34 is also provided with a slight indentation 40 even with the recesses 36. It will be understood in connection with the cross-sectional views of FIGS. 3 and 4 that these are only intended to show the overall configuration of the filter and not to include any showing of the detailed internal construction thereof, which is not of significance relative to the present invention.

The filter retainer shown in the present drawings, particularly with reference to FIG. 5, includes a formed plastic sheet element 16 and two side portions 20 and 22. These two side portions 20 and 22 are provided with recesses 24 and 26 which are of the proper diameter or size to receive intravenous tubing, such as the tube 28 as shown in FIG. 1. In practice, the recesses 24 and 26 may be approximately one-eighth of an inch wide to accommodate intravenous tubing having a diameter of three thirty-seconds of an inch (3/32").

The plastic sheet element 16 is provided with a central generally rectangular longitudinally extending recess or raised portion 44 designed to closely fit over the body of the filter 14. The raised portion 44 of the plastic member 16 is provided with a central rounded portion 46 to accommodate the central passageway 34 of the filter (see FIG. 2), and a pair of inwardly extending ribs 48 and 50 which mate with the recesses 36 and 38, respectively, in the filter body. In addition, the slight protrusion 52 may be provided in the sheet material element 16 to mate with the recess 40.

Small Velcro type pads 54 and 56, including a series of fine hooks may be provided on the two side portions 20 and 22, respectively, of the plastic sheet element 16. A foam band or strap 18 may be secured by pressure to the Velcro tabs 54 and 56 to hold the intravenous filter and the filter retainer in place on the outside of a person's arm, as generally shown in FIG. 1. The Velcro type pads 54 and 56, and the foam band 18 for use therewith may be purchased from a number of suppliers, including Smalley and Bates, Inc. of 220 Little Falls Road, Cedar Grove, N.J. 07009. In the event of infiltration or swelling of a limb, the foam band 18 will release from one of the pads 54 or 56, thereby avoiding injury to the limb.

Incidentally, for completeness, it may be noted that the plastic sheet retaining element is only a few thousandths of an inch, and less than 1/64 of an inch in thickness; and that it is about 3 to 3½ inches across, and about two to two and one-half inches from top to bottom along the central recess. In addition, the main central recess is about 1 3/16 inch wide.

It is to be understood that the foregoing detailed description and the accompanying drawings illustrate one preferred embodiment of the invention. However, certain departures from the construction shown and described hereinabove may be made. Thus by way of example, and not of limitation, in the event that other intravenous filter configurations are employed, the plastic sheet material may be configured to retain such other types of filters by modifying its construction to engage irregularities or to overly the ends of the filter, whereby its engagement with and maintenance of the filter in position is assured. In addition, instead of the use of Velcro securing means, other quickly releasable securing arrangements may be provided for at least one, and possibly for both ends of the strap. Accordingly, the present invention is not limited to the embodiment precisely as shown and described hereinabove.

What is claimed is:

1. An intravenous filter retainer assembly, for use with standard I.V. filters of the elongated, generally rectangular type having one substantially flat side, and one side provided with a raised longitudinally extending passageway and with at least one transverse groove, the filter retainer assembly comprising:

a thin piece of medically inert, formed plastic sheet material;

said sheet material being made of semi-rigid material preformed to have (1) a central recessed portion having an inner configuration conforming to the outer configuration of the filter, (2) a generally rectangular raised portion, (3) a rounded central recess to conform to the raised passageway of the filter, and (4) at least one transverse detent to fit into the transverse groove in said filter, to hold the filter to the retainer;

said sheet material having outer side portions which are relatively flat, but are provided with longitudinally extending grooves approximately one-eighth inch in width to accommodate I.V. tubes;

securing tabs cemented onto said side portions of said plastic sheet material; and foam band retaining strap means free of active adhesive material for releasable engagement with said securing tabs to hold said retainer onto the body of a patient;

said filter retainer assembly weighing less than one quarter of an ounce;

whereby the use of adhesive tape with its potentially adverse effects on patients is avoided, in holding said filter to the patient.

2. An intravenous filter retainer assembly as defined in claim 1 wherein said securing tabs include fine, protruding hook-like means for releasably holding said foam band.

3. An intravenous filter retainer assembly as defined in claim 1 wherein said sheet material is in the order of about 3 to 3½ inches across and about 2 to 2½ inches as measured along the central recess.

4. An intravenous filter retainer assembly as defined in claim 1 wherein said central recess is in the order of one to one and one-half inches in width.

5. An intravenous filter retainer assembly as defined in claim 1 wherein said plastic sheet material is formed of polyethylene terephthalate glycol.

6. An intravenous filter retainer assembly as defined in claim 1 wherein said sheet material is less than 1/64 inch thick.

7. An intravenous filter retainer assembly, for use with standard I.V. filters of the elongated, generally rectangular type having one substantially flat side, and one side provided with a raised longitudinally extending passageway and with at least one transverse groove, the filter retainer assembly comprising:

a thin piece of medically inert, formed plastic sheet material;

said sheet material being formed of semi-rigid material preformed to have a central recessed portion having an inner configuration conforming to the outer configuration of the filter, preformed to have a generally rectangular raised portion, a rounded central recess to conform to the raised passageway, and preformed to have at least one transverse detent to fit into the transverse groove in said filter, to hold the filter to the retainer;

said sheet material having outwardly extending side portions;

securing tabs cemented onto the side portions of said plastic sheet material; and adhesive-free foam band retaining strap means for releasable engagement with said securing tabs;

said filter retainer assembly weighing less than one quarter of an ounce;

whereby the use of adhesive tape with its potentially adverse effects on patients is avoided, in holding said filter to the patient.

* * * * *